(12) United States Patent
Urbanski et al.

(10) Patent No.: US 12,369,970 B2
(45) Date of Patent: Jul. 29, 2025

(54) EPICARDIAL ACCESS SYSTEM AND METHODS

(71) Applicant: BOSTON SCIENTIFIC MEDICAL DEVICE LIMITED, Galway (IE)

(72) Inventors: John Paul Urbanski, Toronto (CA); Brock Miller, Toronto (CA); Rund Abou-Marie, Mississauga (CA)

(73) Assignee: Boston Scientific Medical Device Limited, Galway (IE)

( * ) Notice: Subject to any disclaimer, the term of this patent is extended or adjusted under 35 U.S.C. 154(b) by 50 days.

(21) Appl. No.: 18/453,585

(22) Filed: Aug. 22, 2023

(65) Prior Publication Data

US 2023/0389980 A1 Dec. 7, 2023

Related U.S. Application Data

(63) Continuation of application No. 17/014,144, filed on Sep. 8, 2020, now Pat. No. 11,766,290, which is a
(Continued)

(51) Int. Cl.
*A61B 18/14* (2006.01)
*A61B 17/3207* (2006.01)
(Continued)

(52) U.S. Cl.
CPC ...... *A61B 18/1477* (2013.01); *A61B 18/1492* (2013.01); *A61B 2017/320791* (2013.01);
(Continued)

(58) Field of Classification Search
CPC ............ A61B 18/1477; A61B 18/1492; A61B 17/3417; A61B 2017/320791;
(Continued)

(56) References Cited

U.S. PATENT DOCUMENTS

| 175,254 A | 3/1876 | Oberly |
| 827,626 A | 7/1906 | Gillet |

(Continued)

FOREIGN PATENT DOCUMENTS

| JP | 2015-128637 A | 7/2015 |
| JP | 2015-518752 A | 7/2015 |

(Continued)

OTHER PUBLICATIONS

First Office Action (Notice of Reasons for Rejection) for Japanese counterpart to parent application Japanese Patent Application 2018-510111.

(Continued)

*Primary Examiner* — Michael F Peffley
(74) *Attorney, Agent, or Firm* — Nelson Mullins Riley & Scarborough LLP

(57) ABSTRACT

A method and apparatus are disclosed for a needle for gaining access to the pericardial cavity of a heart. The needle includes an elongate member (e.g. a main shaft) defining a lumen and a side-port in fluid communication with the lumen; a blunt atraumatic tip for delivering energy for puncturing tissue; and a guiding surface (e.g. a ramp) for directing a device (e.g. a guidewire) through the side-port. The method includes using the needle for tenting a pericardium and delivering energy for puncturing the pericardium, and advancing a guidewire or other device through the needle and into the pericardial cavity.

20 Claims, 9 Drawing Sheets

Related U.S. Application Data continuation of application No. 15/754,030, filed as application No. PCT/IB2016/055404 on Sep. 9, 2016, now Pat. No. 10,779,883.

(60) Provisional application No. 62/216,059, filed on Sep. 9, 2015.

(51) Int. Cl.
    *A61B 17/34* (2006.01)
    *A61B 18/00* (2006.01)
    *A61B 90/00* (2016.01)

(52) U.S. Cl.
    CPC . *A61B 17/3417* (2013.01); *A61B 2018/00083* (2013.01); *A61B 2018/00196* (2013.01); *A61B 2018/00351* (2013.01); *A61B 2018/00363* (2013.01); *A61B 2018/00577* (2013.01); *A61B 2018/00601* (2013.01); *A61B 2090/3966* (2016.02)

(58) Field of Classification Search
    CPC .......... A61B 2018/00083; A61B 2018/00196; A61B 2018/00351; A61B 2018/00363; A61B 2018/00577; A61B 2018/00601; A61B 2090/3966
    See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,774,949 A | 10/1988 | Fogarty |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,007,908 A | 4/1991 | Rydell |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,163,921 A | 11/1992 | Feiring |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,558,673 A | 9/1996 | Edwards et al. |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,827,216 A | 10/1998 | Igo et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,972,013 A | 10/1999 | Schmidt |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |

(56) References Cited

U.S. PATENT DOCUMENTS

| | | |
|---|---|---|
| 6,117,131 A | 9/2000 | Taylor |
| 6,142,992 A | 11/2000 | Cheng et al. |
| 6,146,380 A * | 11/2000 | Racz ............... A61N 1/0551 |
| | | 606/41 |
| 6,155,264 A | 12/2000 | Ressemann et al. |
| 6,156,031 A | 12/2000 | Aita et al. |
| 6,162,195 A | 12/2000 | Igo et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,423,051 B1 | 7/2002 | Kaplan et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,666,844 B1 | 12/2003 | Igo et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,770,070 B1 | 8/2004 | Balbierz |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,166,104 B2 | 1/2007 | Young et al. |
| 7,191,015 B2 | 3/2007 | Lamson et al. |
| 7,229,438 B2 | 6/2007 | Young |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,736,347 B2 | 6/2010 | Kaplan et al. |
| 7,797,059 B1 | 9/2010 | Bornzin et al. |
| 7,828,796 B2 | 11/2010 | Wong et al. |
| 7,846,088 B2 | 12/2010 | Ness |
| 7,900,928 B2 | 3/2011 | Held et al. |
| 8,192,425 B2 | 6/2012 | Mirza et al. |
| 8,211,084 B2 | 7/2012 | Kassab et al. |
| 8,241,276 B2 * | 8/2012 | Epstein ............... A61N 1/06 |
| | | 606/41 |
| 8,257,323 B2 | 9/2012 | Joseph et al. |
| 8,282,565 B2 | 10/2012 | Mahapatra et al. |
| 8,311,648 B1 | 11/2012 | Chitre et al. |
| 8,317,810 B2 | 11/2012 | Stangenes et al. |
| 8,388,549 B2 | 3/2013 | Paul et al. |
| 8,475,468 B2 | 7/2013 | Leckrone et al. |
| 8,500,697 B2 | 8/2013 | Kurth et al. |
| 8,538,555 B1 | 9/2013 | Chitre et al. |
| 8,603,031 B2 | 12/2013 | Callas et al. |
| 8,874,237 B2 | 10/2014 | Schilling |
| 8,906,056 B2 | 12/2014 | Gillies et al. |
| 8,979,842 B2 | 3/2015 | McNall et al. |
| 8,986,278 B2 | 3/2015 | Fung et al. |
| 9,131,960 B2 * | 9/2015 | Racz ............... A61B 17/3478 |
| 9,179,962 B2 * | 11/2015 | Fischell ............... A61B 90/39 |
| 10,136,937 B1 * | 11/2018 | Cosman, Jr. ....... A61B 18/1477 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0187461 A1 | 10/2003 | Chin |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |

(56) References Cited

U.S. PATENT DOCUMENTS

| | | |
|---|---|---|
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0261673 A1 | 11/2005 | Bonner et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Mdlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2007/0293924 A1 | 12/2007 | Belden et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0171304 A1 | 7/2009 | Cao et al. |
| 2009/0177114 A1 | 7/2009 | Chin et al. |
| 2009/0198252 A1 | 8/2009 | Seifert et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0331854 A1 | 12/2010 | Greenberg et al. |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0095434 A1 | 4/2012 | Fung et al. |
| 2012/0130366 A1 | 5/2012 | Carroll et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0085388 A1* | 4/2013 | Stangenes ............ A61B 8/12 606/170 |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2015/0216620 A1* | 8/2015 | Davies ............ A61B 90/39 606/41 |
| 2016/0220741 A1 | 8/2016 | Garrison et al. |
| 2016/0242661 A1 | 8/2016 | Fischell et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| WO | 99/04851 A1 | 2/1999 |
| WO | 2014/141197 A1 | 9/2014 |
| WO | 2015/114560 A1 | 8/2015 |
| WO | 2015/130987 A1 | 9/2015 |

OTHER PUBLICATIONS

First Office Action for Chinese counterpart to parent application Chinese Patent Application 2016800519082.

International Search Report and Written Opinion received for PCT Patent Application No. PCT/IB2016/055404, mailed on Dec. 8, 2016, 11 pages.

Patent Cooperation Treaty, International Preliminary Report on Patentability, International Application No. PCT/IB2016/055404, dated Dec. 8, 2016.

Supplementary Partial European Search Report for counterpart to parent application European Application No. EP16843791, dated Apr. 30, 2019.

* cited by examiner

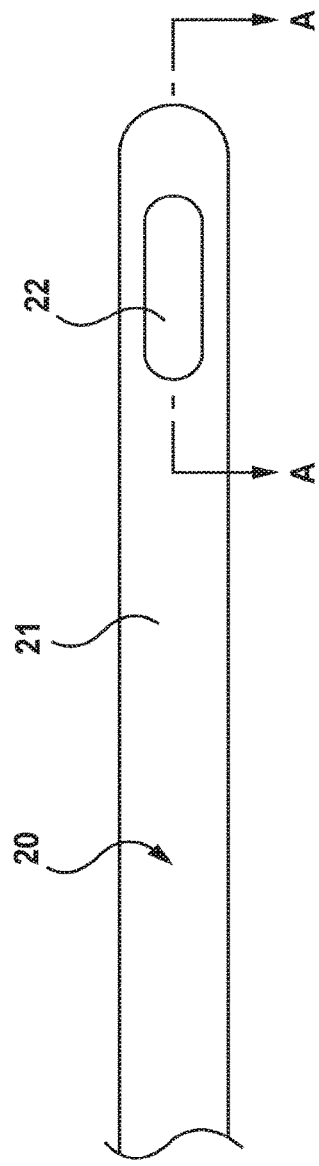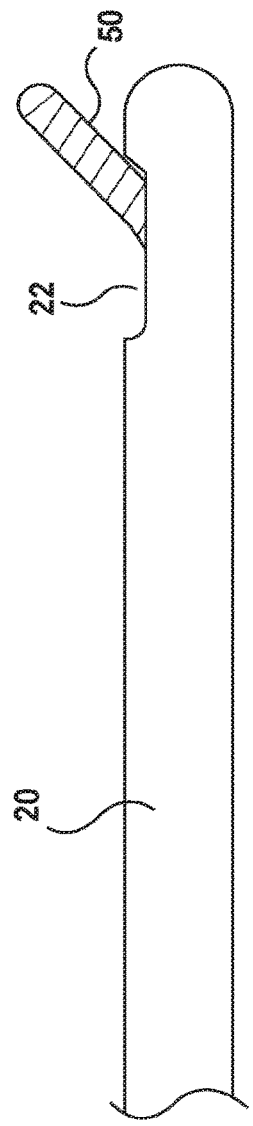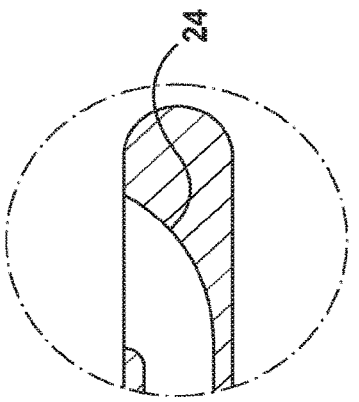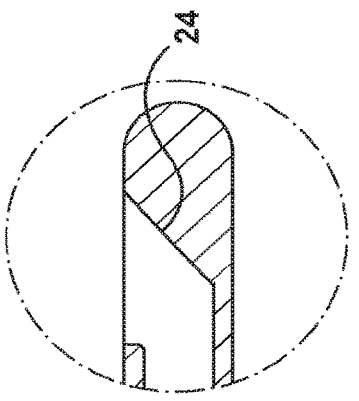
FIG. 1A
FIG. 1B
Detail A-V2
Detail A-V1

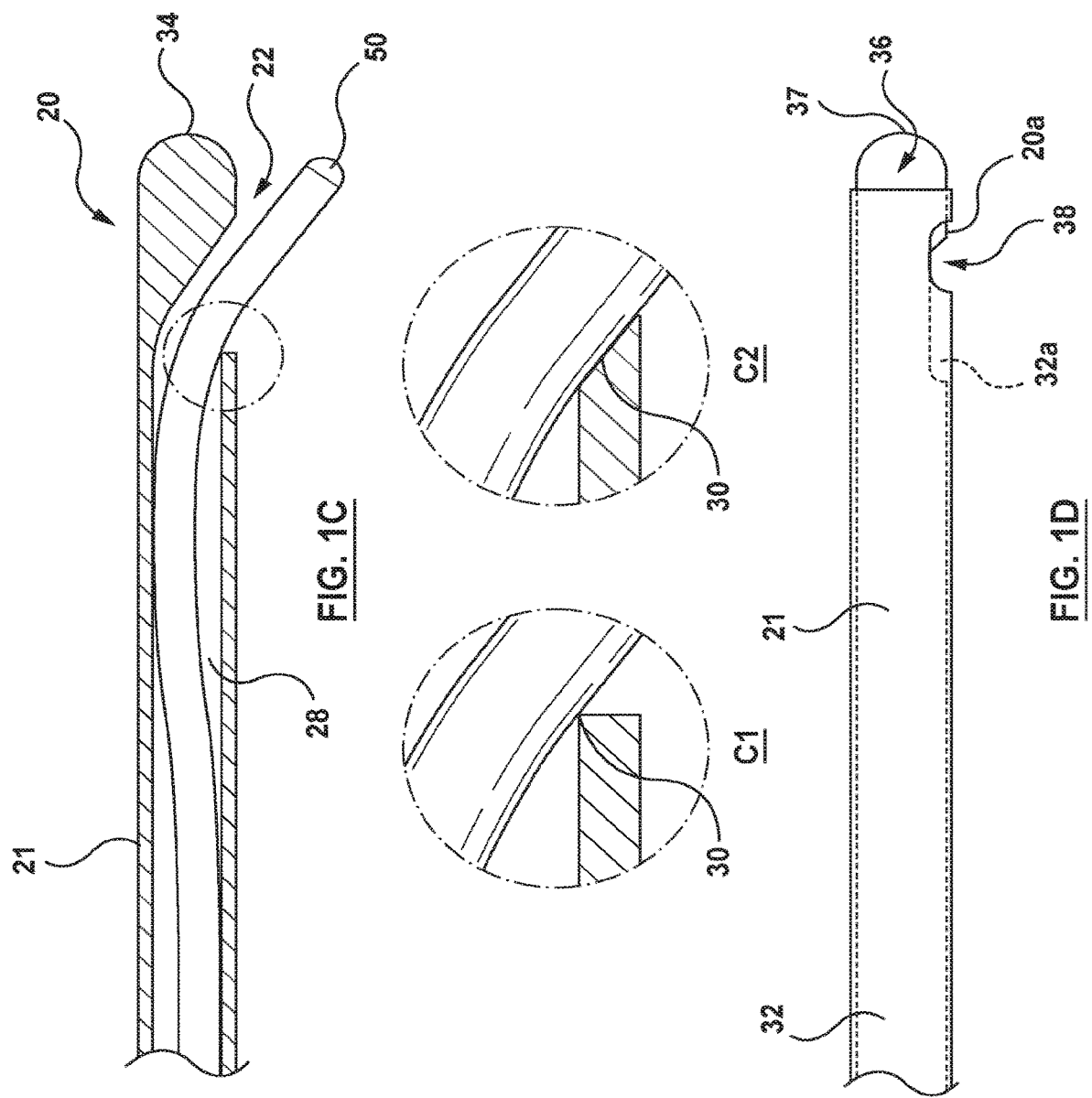

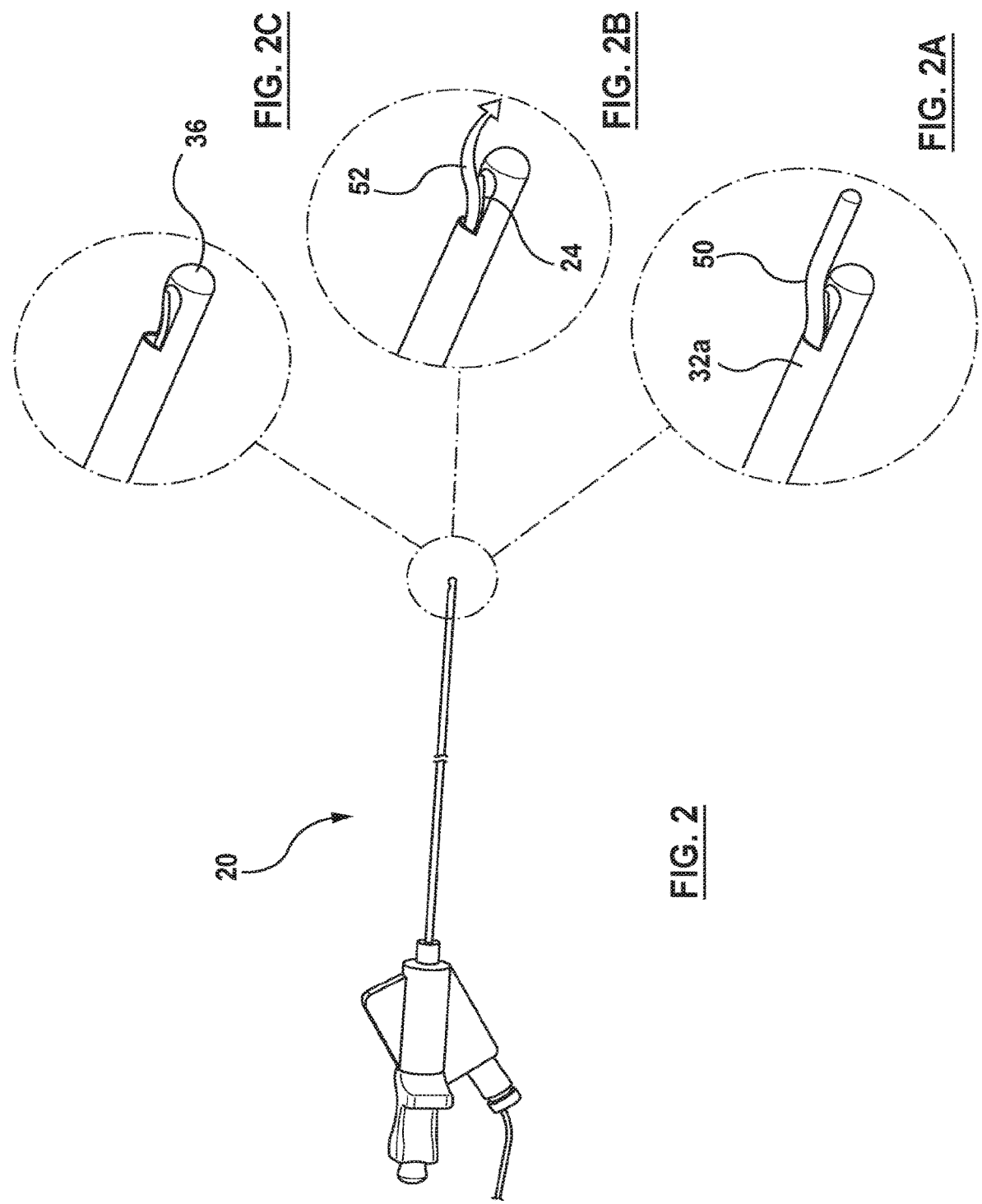

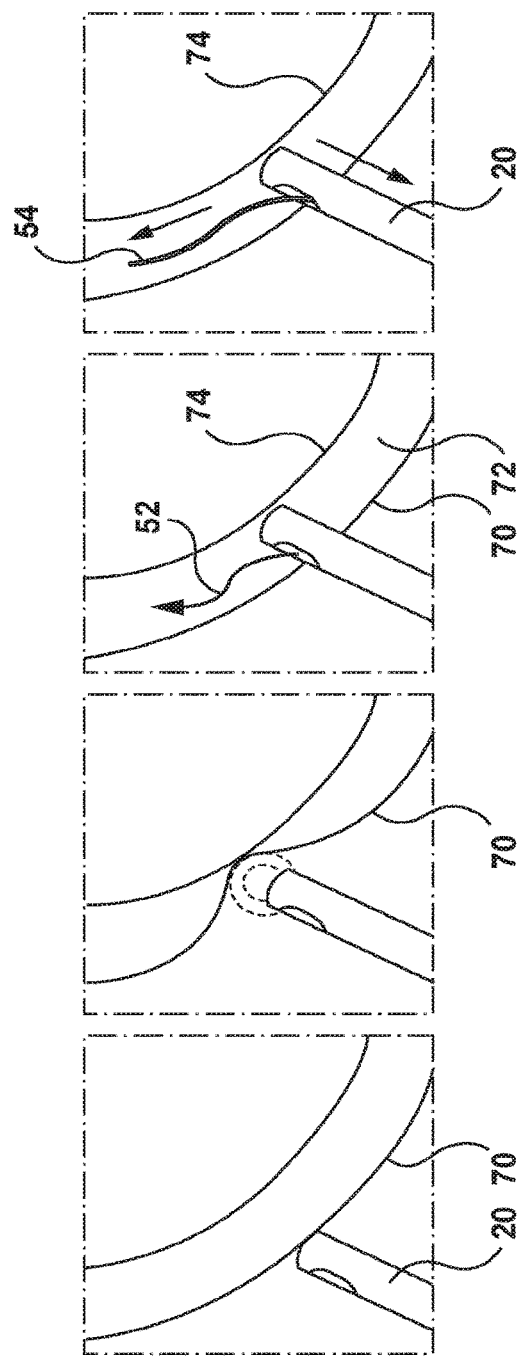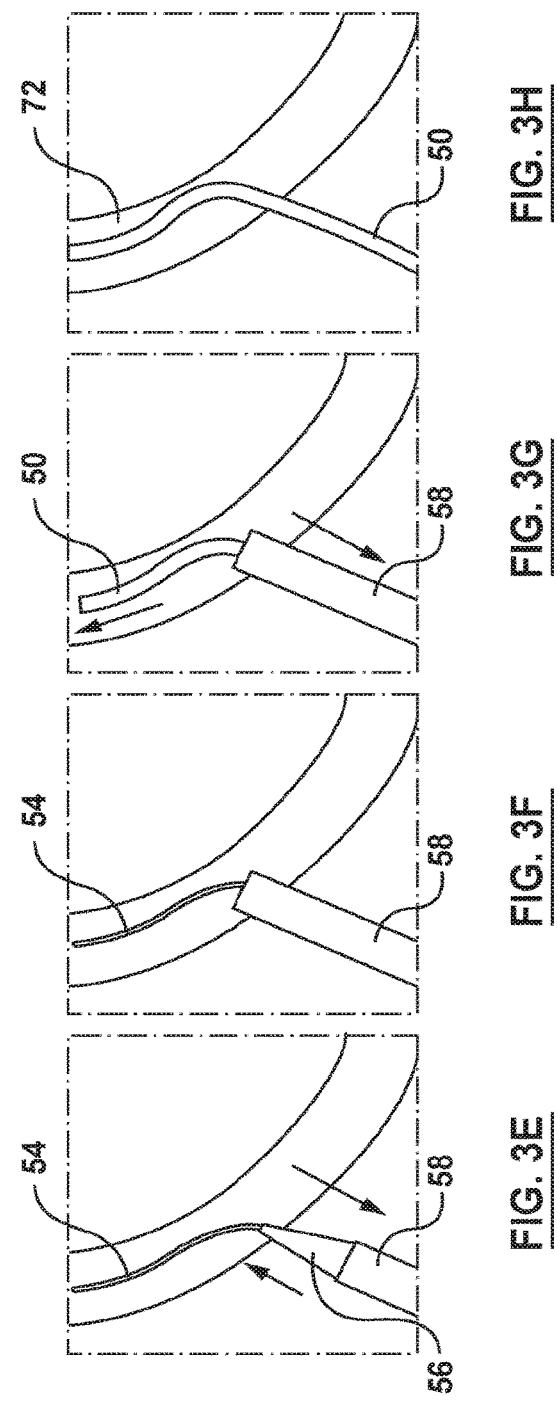

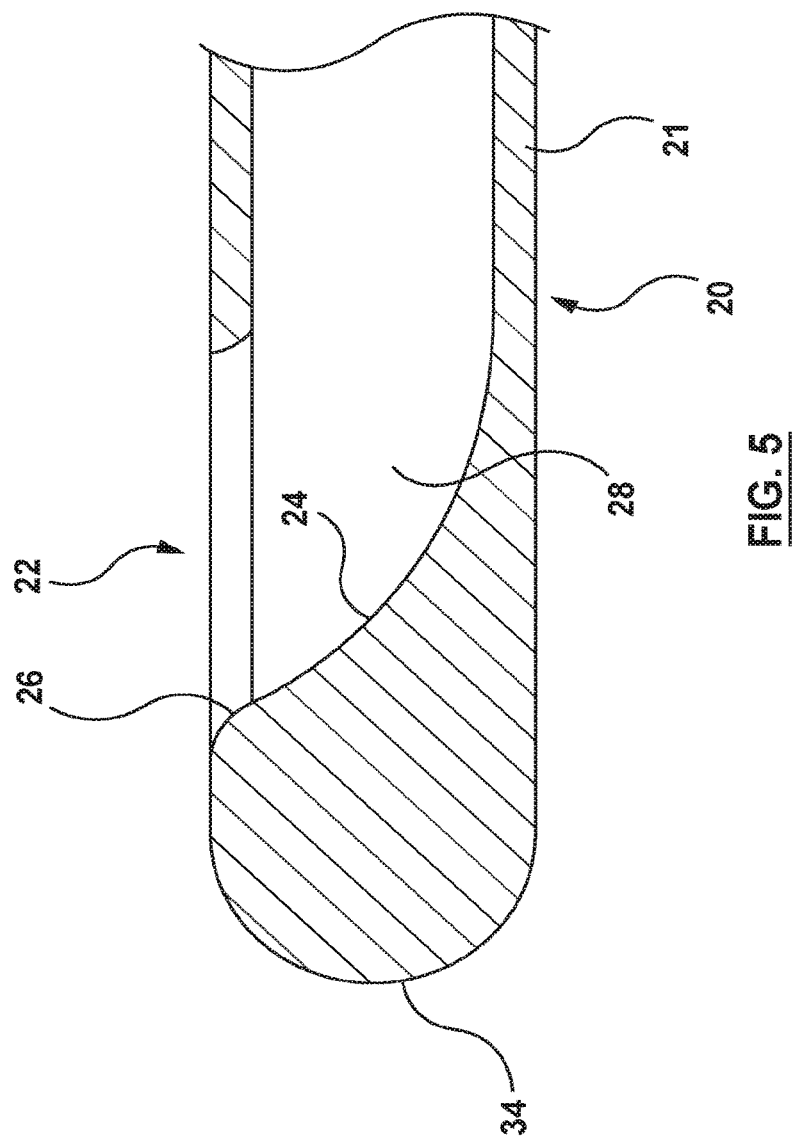

EPICARDIAL ACCESS SYSTEM AND METHODS

CROSS-REFERENCE TO RELATED APPLICATIONS

This application is a continuation of and claims the benefit of U.S. patent application Ser. No. 17/014,144, entitled "EPICARDIAL ACCESS SYSTEM AND METHODS," and filed Sep. 8, 2020, now U.S. Pat. No. 11,766,290, issued Sep. 26, 2023, which is a continuation of and claims the benefit of U.S. patent application Ser. No. 15/754,030, entitled "EPICARDIAL
ACCESS SYSTEM & METHODS," and filed Feb. 21, 2018, now U.S. Pat. No. 10,779,883,issued Sep. 22, 2022, which is a national stage entry of International Application No. PCT/IB2016/055404, entitled "EPICARDIAL ACCESS SYSTEM & METHODS," filed Sep. 9,2016, which claims the benefit of U.S. Provisional Application No. 62/216,059, entitled "EPICARDIAL ACCESS SYSTEM AND METHODS," and filed Sep. 9, 2015, which are hereby incorporated by reference in their entireties.

TECHNICAL FIELD

This disclosure relates to the field of surgical needles. More specifically, this disclosure relates to surgical needles that use energy for puncturing.

BRIEF DESCRIPTION OF THE DRAWINGS

In order that the invention may be readily understood, embodiments of the invention are illustrated by way of examples in the accompanying drawings, in which:

FIG. 1, consisting of FIGS. 1A-1D, as well as detail views A-V1, A-V2, C1 and C2, is an illustration of a needle having a side-port in accordance with an embodiment of the invention;

FIG. 2, including detail views 2A-2C, is an illustration of a needle having a side-port in accordance with an alternative embodiment of the invention;

FIG. 3, consisting of FIGS. 3A-3H, is an illustration showing the steps in a method of using a needle in accordance with an embodiment of the invention;

FIG. 5 is an illustration showing an enlarged view of a side-port in accordance with an embodiment of the invention;

DETAILED DESCRIPTION

Figure 4A:
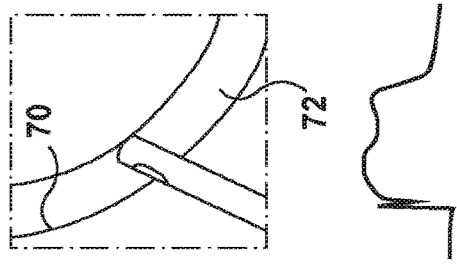
FIG. 4, consisting of FIGS. 4A-4F, is an illustration showing the use of ECG in accordance with an embodiment of the invention.

Minimally invasive access to the pericardial space is required for diagnosis and treatment of a variety of arrhythmias and other conditions. Access to the space may be initiated using a large diameter (for example, about 17Ga) Tuohy-style needle via the subxiphoid approach. A guidewire (for example, about 0.032 inches (about 0.81 mm) in outer diameter) is then advanced to the heart through the needle lumen. After gaining access to the pericardial space, the operator removes the Tuohy needle then advances and secures a sheath (for example, 8.5Fr) to facilitate use of treatment devices such as ablation and mapping catheters.

Mechanical puncture using large bore needles, as described above, is associated with a high clinical complication rate. Although the stiff needle provides some stability and some tactile feedback to the user, unwanted tissue damage is possible if the needle inadvertently punctures or unintentionally lacerates tissue.

As a consequence of the challenges and uncertainties of using mechanical puncture for accessing the pericardial space, physicians may resort to common endocardial ablation in situations where epicardial ablation is a preferred treatment, such as ventricular tachycardias. New devices or methods to improve the safety and predictability of gaining access to the pericardial space would be of benefit.

The problem of improving the ease of use, safety, and predictability of gaining access to the epicardium is solved, at least in part, by a needle for gaining epicardial access, the needle having an elongate member (e.g. a main shaft) defining a lumen and a side-port in fluid communication with the lumen; a blunt atraumatic tip for delivering energy for puncturing tissue; and a guiding surface (e.g. a ramp) for directing a device (e.g. a guidewire) through the side-port.

The present inventors have conceived, and reduced to practice, embodiments of such a medical device. Some embodiments of the needle have a blunt tip of 17, 18, 19, or 19.5Ga. The blunt tip prevents any premature mechanical puncture to the pericardium when pressed against it. Also, a needle with a blunt tip provides better tactile feedback than a needle with a sharp tip. The side-port allows delivery of contrast agent and facilitates deployment of a device (e.g. a guidewire) through the needle to confirm access to the pericardial space. Physicians typically use fluoroscopy to check that the guidewire (or other device) is wrapped around the heart to confirm pericardial access. Physicians may also confirm access via tactile feedback which may indicate incorrect needle position or obstruction. Physicians may also deliver contrast medium to confirm access and determine needle location.

In a first broad aspect, embodiments of the present invention comprise a needle for use with a device and for gaining epicardial access, the needle comprising: an elongate member which is comprised of a metal and defines a lumen and a side-port with a proximal edge, the side-port being in fluid communication with the lumen; an insulation covering an outside of the elongate member wherein a blunt tip of the needle is electrically exposed to define an electrode for delivering energy for puncturing tissue; a guiding surface extending from a side wall of the elongate member which is opposite to the side-port to define an end of the lumen, the guiding surface being configured for directing the device through the side-port; and an insulation portion covering a proximal part of the side-port defined by the elongate member to define an aperture which is smaller than the side-port, wherein the insulation portion is comprised of a polymer that is softer and less abrasive than the metal of the proximal edge.

As a feature of the first broad aspect, the needle is configured for delivering energy through a metal side wall of elongate member to the electrode. In some embodiments of this feature, the electrode has greater radiopacity than the elongate member. Some embodiments further comprise insulation on an inner surface of the elongate member adjacent to the side-port to reduce electrical leakage. Some embodiments include insulation on an inner surface of most or substantially all the elongate member to reduce electrical leakage. In some embodiments of this feature, a part of the elongate member adjacent and distal of the side-port is electrically exposed to define an elongate member exposed portion. Some examples include a distal edge of the side-port is located at a distance of about 0.050 to 0.125 inches (about 1.27 to 3.18 mm) from an electrode distal tip. In some such examples, the distal edge of the side-port is located at a distance of about 0.090 inches (about 2.29 mm) from the electrode distal tip.

In typical embodiments of the first broad aspect, the insulation portion is configured to reduce abrasive friction between the device and the proximal edge of the side-port as the device is advanced through the side-port. In typical embodiments, the lumen terminates at the side-port. Typical embodiments include the needle comprising a single side-port operable for the device to travel therethrough. In some embodiments of the first broad aspect, the side-port is capsule-shaped. In some examples, a distal edge of the side-port includes a bevel. In some such examples, the bevel includes a combination of rounded and flat portions.

In some embodiments of the first broad aspect, the proximal edge of the side-port is beveled. In some embodiments, the guiding surface has a generally S-shaped surface.

As another feature of the first broad aspect, a distal end of the guiding surface is beveled, whereby the insulation portion which covers a proximal part of the side-port and the distal end of the guiding surface facilitate the device being guided out of a side of the needle and in a forward direction when advanced out of the side-port.

In accordance with an embodiment of the present invention, a method is disclosed for accessing a pericardial cavity, the method comprising the steps of: (1) contacting a pericardium with a needle, (2) tenting the pericardium with the needle and delivering energy through a blunt tip of the needle, (3) puncturing the pericardium with the needle and injecting a contrast flow into a pericardial cavity through a side-port of the needle, (4) advancing a guidewire through the needle and into the pericardial cavity, and (5) withdrawing the needle while leaving the guidewire in the pericardial cavity.

In accordance with an embodiment of the present invention, a method is disclosed for accessing a pericardial cavity, the method comprising the steps of: (1) contacting a pericardium with a needle, (2) tenting the pericardium with the needle and delivering energy through a blunt tip of the needle, (3) puncturing the pericardium with the needle and injecting a contrast flow into a pericardial cavity through a side-port of the needle, (4) advancing a small diameter guidewire into the pericardial cavity, (5) withdrawing the needle and advancing a dilator to dilate the puncture through the pericardium, (6) advancing a sheath over the dilator into pericardial cavity, (7) withdrawing the small diameter guidewire and advancing a relatively larger guidewire into the pericardial cavity, and (8) withdrawing the sheath.

In a further broad aspect, embodiments of the present invention are for a method having the steps of contacting a pericardium with a needle, using the needle for tenting the pericardium and delivering energy, using the needle for puncturing the pericardium and injecting a contrast flow into a pericardial cavity, advancing a guidewire (or other device) through the needle and into the pericardial cavity, and withdrawing the needle while leaving the guidewire (or other device) in the pericardial cavity.

As features of this aspect, some embodiments of the method further include the steps of advancing a mapping catheter or some other diagnostic device, and/or advancing an ablation catheter or some other treatment device, and/or placing leads or other medical devices.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1A shows a top view of a needle 20 having a side-port 22 in elongate member 21. FIG. 1B shows a side view of the same needle with a guidewire 50 extending out of side-port 22. The side-port of FIGS. 1A and 1B is a slotted hole. The dimensions of the slot are dependent on the needle gauge and guidewire outer diameter. Some embodiments of needle 20 are 17Ga, have a side-port width of about 0.036 inches (about 0.91 mm), a radius of about 0.018 inches (about 0.46 mm), a slot length of about 0.180 inches (about 4.57 mm), and can accommodate deployment and retraction of a 0.032 inches (about 0.81 mm) guidewire, and of guidewires having a smaller outer diameter. Such an embodiment may also accommodate, with a smaller clearance, a guidewire with an outer diameter of 0.035 inches (about 0.89 mm). Guidewires used in the disclosed method are typically comprised of spring stainless steel. In some embodiments, the distal tip of the guidewire is made of nitinol to provide a softer tip than steel. Some alternative embodiments comprise an insulated guidewire having a lubricous coating on the insulation. Embodiments of needle 20 typically have only a single side-port operable for advancing a guidewire (or another device) therethrough.

While this disclosure, for explanatory purposes, focuses on the use of needle 20 with guidewires, other devices can be advanced through needle, for example, flexible devices operable to delivery energy or monitor physiological variables.

The embodiment of the side-port 22 of FIG. 1A is a rounded slot or a slotted hole (i.e. capsule-shaped) having a constant side-port width. This configuration provides a flat wall with a minimal edge profile, thereby reducing the potential for generating debris when deploying or retracting a guidewire. Typically, side-port 22 and guidewire 50 are configured such that the clearance of the side-port 22 from the guidewire will be at least about 0.001 inches (about 0.025 mm). If using a smaller outer diameter guidewire, the clearance will be greater.

Detail A-V1 and detail A-V2 show alternative views for cut-away line A-A of FIG. 1A. Details A-V1 and A-V2 illustrate a guiding surface 24 (or ramp) within side-port 22, which functions to guide an advancing guidewire 50 through side-port 22. The guiding surface embodiment may be straight (e.g. detail A-V1) or curved (e.g. detail A-V2). The portion of guiding surface 24 visible from external side-view (from outside of the needle) has a length of about 0.020 inches (about 0.51 mm) for the embodiment of FIG. 1B. Please note, that while not all of the figures show a layer of insulation since it is not necessary for an understanding of the features illustrated by those figures, typical embodiments of needle 20 include insulation.

Guidewire 50 is placed under a bending moment when exiting the side port. To reduce this force, a bevel 26 (shown in FIG. 5) is located at the distal edge of side-port 22. In some embodiments, a bevel 26 of 10 degrees is located about 0.020 inches (about 0.51 mm) from the distal edge of side-port 22. Some such embodiments have been shown to be effective in reducing the bending moment. In some embodiments the bevel is generally flat, while in other embodiments the bevel is rounded, and in yet further embodiments the bevel includes a combination of rounded and flat portions.

FIG. 5 is a cut-away view including distal tip 34 of needle 20, wherein elongate member 21 defines lumen 28, guiding surface 24, and side-port 22. The embodiment of guiding surface 24 of FIG. 5 has a generally S-shaped surface. In general, side-port 22 is located close to the distal tip of the needle, which is advantageous for confirming the position of distal tip 34 because it allows contrast fluid to be delivered close to the needle's tip. In contrast, a device having a side-port that is relatively further away from the tip is more likely to encounter a situation where the side-port is still covered by tissue even though the distal tip has punctured a layer of tissue. A side-port 22 located close to the distal tip, in combination with the previously described bevel 26, also allows for a curved or 'J' tip wire extended through side-port 22 to travel a short distance forward before curving, which prevents potential piercing of the epicardium with the wire tip. While a curved tip wire that easily bends or is floppy at the distal tip is advantageous for reducing unwanted tissue trauma, needle 20 may also be used with guidewire having a straight tip.

FIG. 1C is a cross-section showing a guidewire 50 that has been advanced through the lumen 28 and the side-port of needle 20. Enlarged sections C1 and C2 show guidewire 50 in contact with two different embodiments of the proximal edge 30 of side-port 22. Enlarged section C1 includes a proximal edge 30 having an approximately 90° angle. This angle is sharp enough to scrape a guidewire as it is advanced or retracted through the side-port, which may result in some debris creation. It is advantageous for proximal edge 30 to be beveled (as shown, for example, in enlarged section C2) to reduce debris generation when translating the guidewire through the needle. Some embodiments include a straight beveled edge, or a rounded bevel located about 0.020 inches (about 0.51 mm) from a proximal edge 30. In some such embodiments, these bevels have proven effective in reducing debris formation.

FIG. 1D illustrates needle 20 with insulation 32 (typically a polymer) covering the needle shaft, leaving an area around side-port 22 exposed, and a distal tip area exposed to define an electrode 36 which may be used for channeling into and puncturing tissue. In some alternative embodiments, insulation 32 is a ceramic.

Typical embodiments of needle 20 have an elongate member 21 (i.e. a main shaft) comprised of 304, 316 or 317 stainless steel, and an electrode 36 comprised of the same steel as the elongate member 21, with electrode 36 being dome welded. Alternative embodiments of elongate member 21 are comprised of other metals, including copper, titanium and nickel-titanium alloys, amongst others. In typical embodiments, energy (e.g. electricity) is delivered to electrode 36 through the metal side wall of needle 20. In some alternative embodiments, the needle's elongate member 21 is comprised of a stiff polymer and electrical energy is delivered to electrode 36 through an electrically conductive wire. Some alternative embodiments have an electrode 36 comprised, at least in part, of material more radiopaque than the elongate member such as platinum, platinum and Iridium alloys, gold, or silver to provide radiopaque visibility under fluoroscopy to determine the location of the needle's tip (i.e. the electrode has greater radiopacity than the elongate member). Such materials also improve reduction potential when collecting ECG data. Round tipped electrodes and the use of such round tipped electrodes for cutting tissue is described in U.S. Pat. No. 8,192,425, which is incorporated-by-reference herein in its entirety.

In one specific embodiment of needle 20, side-port 22 in elongate member 21 has a length of about 0.180 inches (about 4.57 mm), the distance between side-port 22 and electrode 36 is about 0.065 inches (about 1.65 mm), electrode 36 has a hemispherical shape with a radius of about 0.025 inches (about 0.64 mm), whereby distal tip 34 of needle 20 has an outer diameter of about 0.050 inches (about 1.25 mm), and there is distance of about 0.090 inches (about 2.29 mm) between electrode distal tip 37 (FIG. 1D) and side-port 22. In alternative embodiments, the distance between side-port 22 and electrode 36 is about 0.5 to 2 times the outer diameter of the needle tip; the length of side-port 22 depends on the inner diameter of the needle and the outer diameter of the an intended guide-wire, and ranges from about 0.1 to 0.2 inches, or about 2.54 to 5.08 mm (about the equivalent of 3 to 6 times the outer diameter of a 0.032 inch (about 0.81 mm) guidewire); the distance between electrode distal tip 37 and side-port 22 ranges from about about 0.050 to 0.125 inches (about 1.27 to 3.18 mm); and the electrode 36 has a size of about 22 to 17 Gauge (about 0.028 inches (about 0.71 mm) to about 0.058 inches (about 1.47 mm)). The electrode is large enough to provide bumper support against heart tissue.

FIG. 1D also illustrates insulation portion 32a, which covers a proximal part of side-port 22 to define an aperture 38 having a length of about 0.039 inches (about 0.99 mm). Aperture 38 is smaller than side-port 22 (uncovered). If contrast fluid is delivered through needle 20 under a constant lumen fluid pressure, the contrast will expel in a narrower stream and closer to the distal tip through an aperture 38 than through a relatively longer side-port 22.

Insulation portion 32a also reduces the amount of abrasive friction between guidewire 50 and proximal edge 30 of the side-port. First, while guidewire 50 can still rub against proximal edge 30 as it travels through the side-port, insulation portion 32a reduces the frictional forces between the guidewire and proximal edge 30. Second, when guidewire 50 travels through the side-port, it glides over insulation portion 32a, which is comprised of a polymer that is softer and less abrasive than the metal of the proximal edge 30. Insulation portion 32a further functions to direct an advancing guidewire forward, as to be further explained below.

In addition, insulation portion 32a reduces electrical leakage through side-port 22. In typical embodiments of needle 20 the tubular metal shaft tube is not insulated, which allows some electricity to leak out of the metal immediately adjacent to the side-port (i.e. metal forming the edge of the side-port), and some electricity to leak through fluid within the lumen and out of side-port 22. Insulation portion 32a covers some of the metal immediately adjacent the side-port to reduce electrical leakage therefrom. Insulation portion 32a also reduces the amount of fluid inside the lumen that is exposed to the environment outside the needle, thereby reducing electrical leakage through the fluid. Some alternative embodiments of needle 20 include insulation on an inner surface of the metal shaft tube in the area of the side-port (i.e. adjacent to) to reduce electrical leakage. Some other alternative embodiments include insulation on an inner surface of most or substantially all the metal shaft tube to reduce electrical leakage.

Another feature of needle 20 illustrated in FIG. 1D is that insulation 32 leaves a part of needle 20 adjacent to side-port 22 exposed to define elongate member exposed portion 20a. Another way to describe elongate member exposed portion 20a is that insulation 32 is trimmed back from the distal edge of side-port 22 to reduce the profile (or surface area) of the distal face of side-port 22. A reduced profile for the distal face allows a guidewire to exit the side-port at a reduced angle, i.e., closer to needle 20. Furthermore, including elongate member exposed portion 20a may help avoid a metallic guidewire adhering to insulation immediately adjacent to the side-port if a physician inadvertently electrifies the guidewire.

Figure 4B:
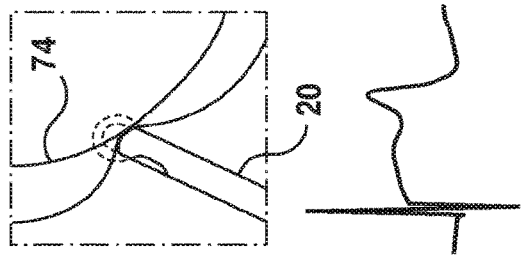
Figure 4C:
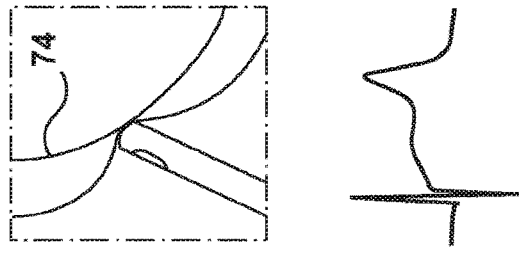
Figure 4D:
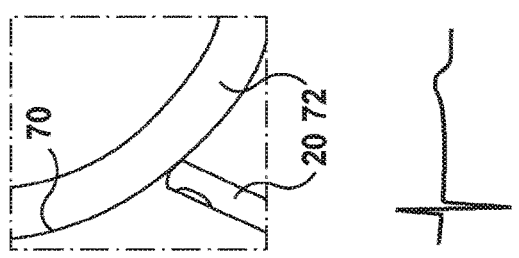
Figure 4E:
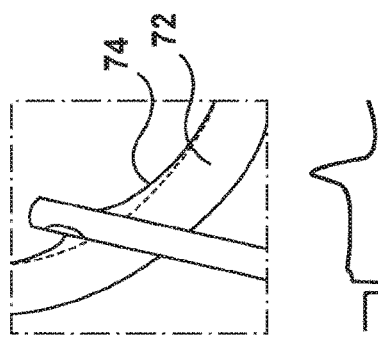
Figure 4F:
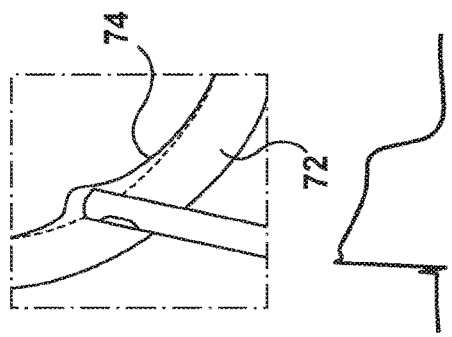
Figure 7A:
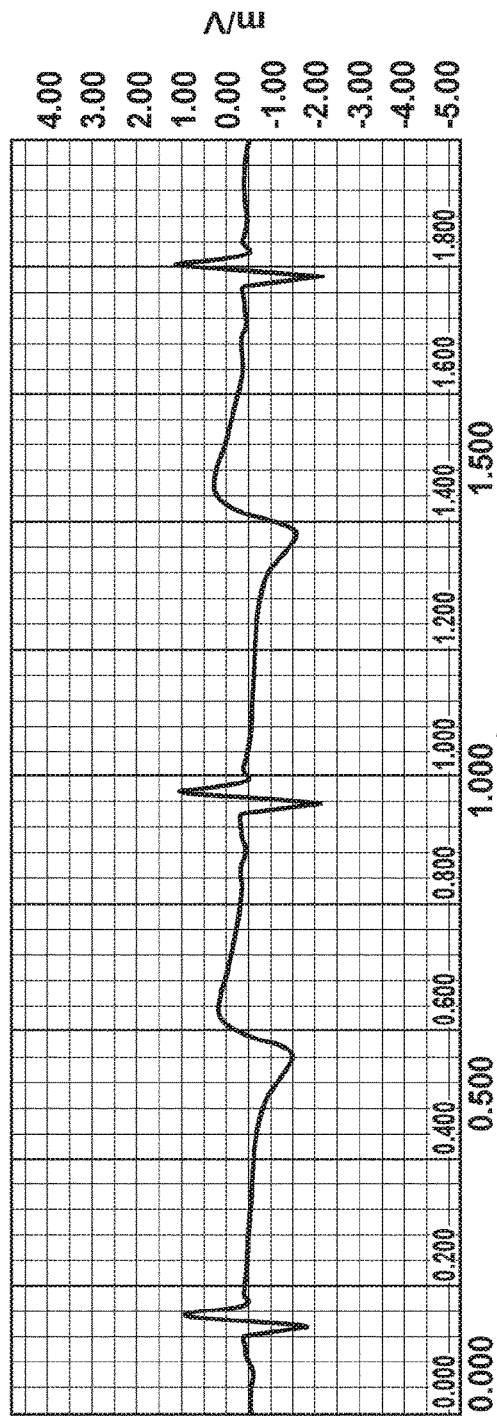
FIG. 7, consisting of FIGS. 7A-7D, shows ECG readings in accordance with an embodiment of the invention.
Figure 7B:
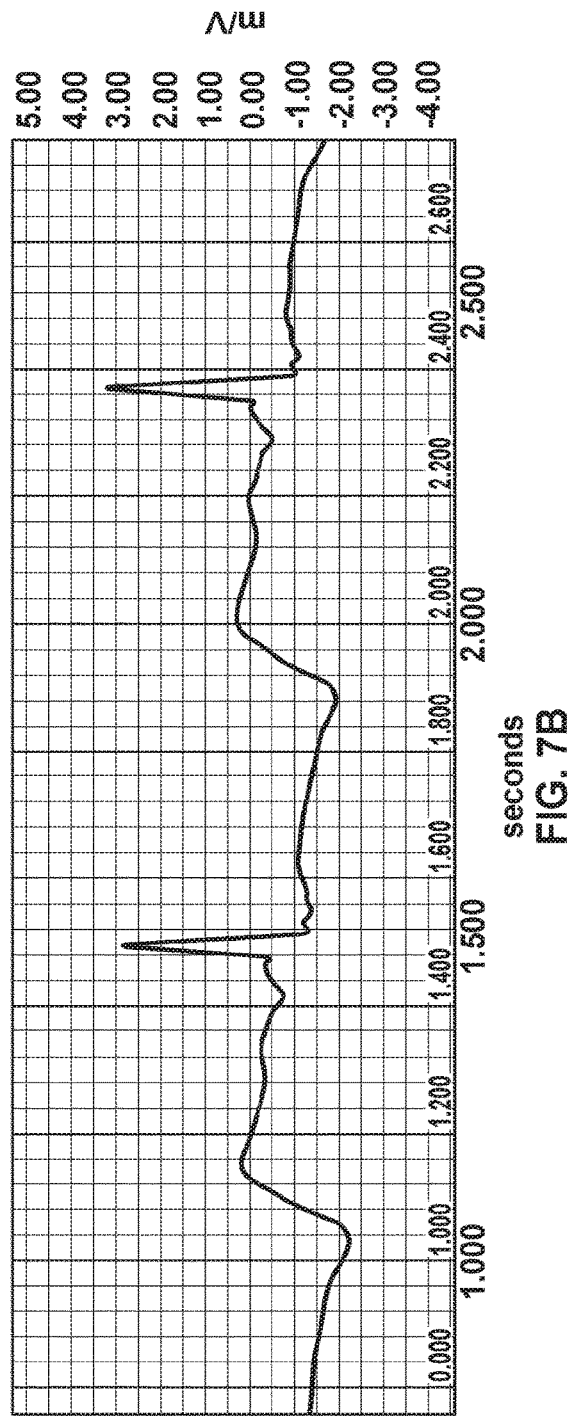
Figure 7C:
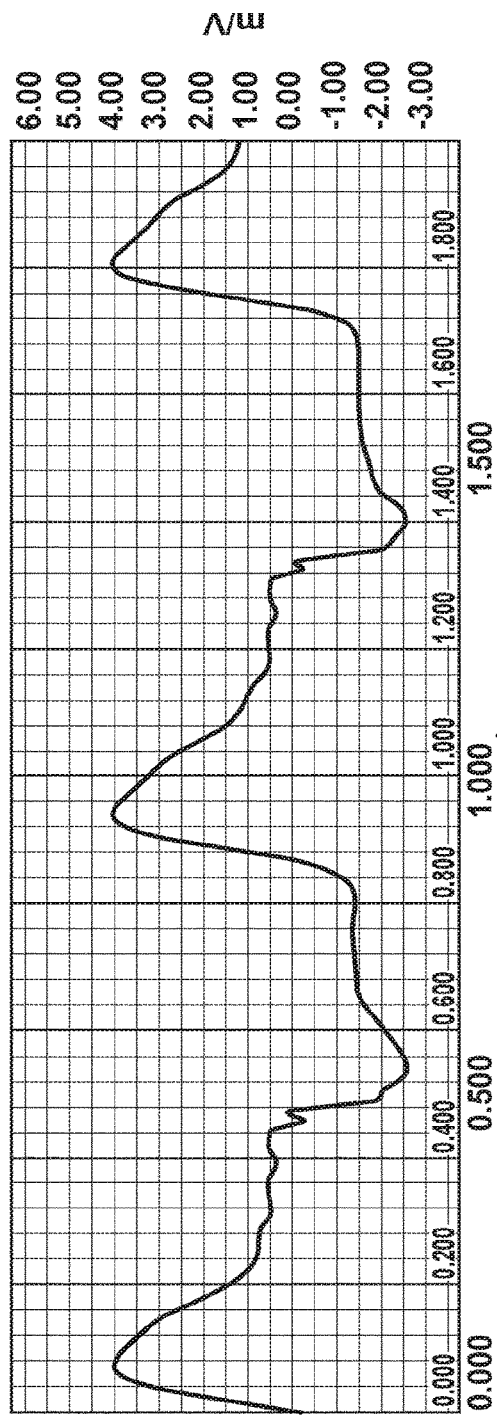
Figure 7D:
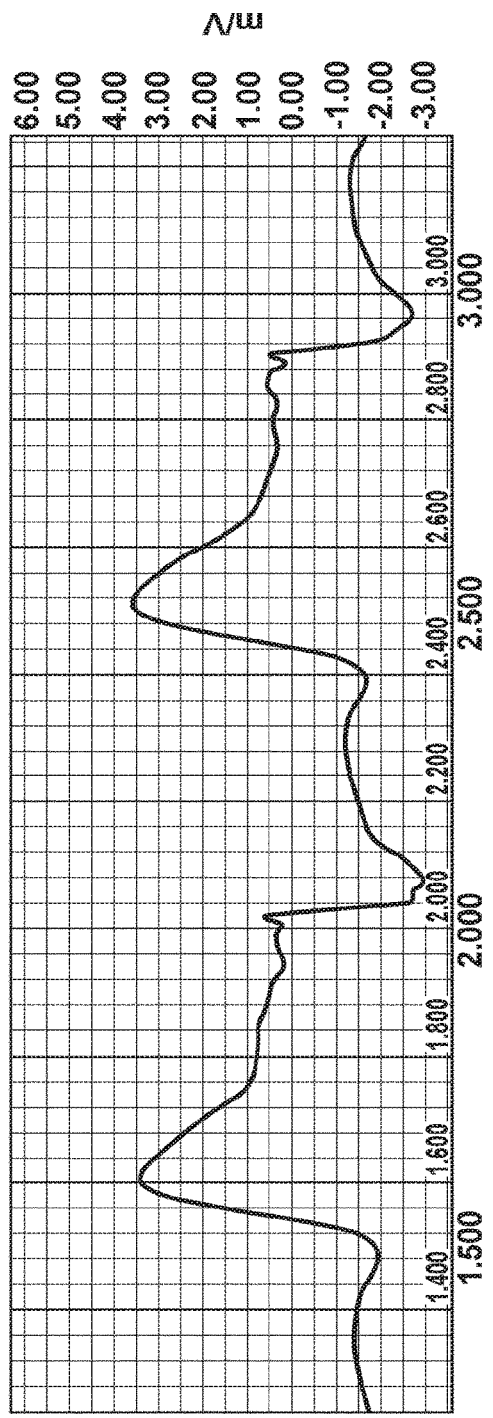

FIG. 2 illustrates an embodiment of needle 20 having a lubricious coating to enhance tactile feedback. FIGS. 2A to 2C show some of the uses of needle 20. FIG. 2A illustrates a guidewire 50 that has been advanced out of the side-port and is being advanced forwards. Guidewire 50 is guided forward by insulation portion 32a and bevel 26 of guiding surface 24. In more detail, the insulation portion 32a covers a proximal part of the side-port and a distal end of the guiding surface (or ramp) is beveled, whereby a device (e.g. a guidewire) is guided out of a side of the needle and in a forward direction when advanced out of the side-port. FIG. 2B illustrates contrast fluid injected using the side-port to create a contrast flow 52. FIG. 3 illustrates that a blunt tip comprised of electrode 36 can be used for ECG monitoring and recording. FIG. 4, consisting of FIGS. 4A-4F, illustrates some monitoring situations and the associated ECG signals. FIG. 7, consisting of FIGS. 7A-7D, shows ECG readings for different locations of the distal tip 34 of needle 20 within a pig to illustrate the advantage of ECG usage in identifying a puncture of a pericardium.

One method to fabricate a distal portion of a needle having the described geometry is to weld a metal billet, placed inside the needle lumen and flush with the needle's distal tip, to the distal end of the needle's metal shaft. The metal billet has a prefabricated guiding surface produced using milling or electrical discharge machining (EDM), and the needle shaft has a prefabricated side-port.

Another method to fabricate a distal portion of a needle is to first weld a solid metal billet flush with the distal tip of the needle's shaft, and then form the side port slot and guiding surface with an EDM electrode having a geometry corresponding to the side port and guiding surface.

FIG. 3 is an illustration showing an eight step method of using five devices, including a needle 20 disclosed herein. FIG. 3A shows a step 1 of contacting a pericardium 70 with needle 20. The heart is typically approached using a subxiphoid approach. Step 2 (FIG. 3B) includes tenting pericardium 70 with the needle and delivering energy (shown in broken line) through the blunt tip of needle 20. Step 3 (FIG. 3C) includes puncturing the pericardium 70 with the needle and injecting a contrast flow 52 into pericardial cavity 72 through a side-port of needle 20. In this example of the method, needle 20 is not touching myocardium 74, while in alternative embodiments, needle 20 touches but does not tent the myocardium 74. FIG. 3D illustrates step 4, advancing a small diameter guidewire 54 through the side-port and into the pericardial cavity 72. After the small diameter guidewire 54 is advanced, the method further includes a step 5 (FIG. 3E) of withdrawing needle 20 and advancing dilator 56 to dilate the puncture through pericardium 70. Sheath 58 may be advanced with dilator 56 or the sheath may be advanced afterwards to arrive at the illustration of FIG. 3E. Once the puncture is dilated, the method includes step 6 of advancing sheath 58 over the dilator into pericardial cavity 72 to arrive at the illustration of FIG. 3F. Step 7 includes withdrawing small diameter guidewire 54 and advancing guidewire 50 into pericardial cavity 72 (FIG. 3G). Step 8 (FIG. 3H) includes withdrawing the sheath, and leaving the guidewire 50 in pericardial cavity 72. In some embodiments guidewire 50 has a diameter of about 0.032 inches (about 0.813 mm) and small diameter guidewire 56 has a diameter of about 0.018 inches (about 0.46 mm). In some alternative embodiments, small diameter guidewire 56 has a diameter smaller than 0.018 inches (about 0.46 mm). Once guidewire 50 has been advanced into pericardial cavity 72 to provide access, other steps may include advancing a mapping catheter or some other diagnostic device, advancing an ablation catheter or some other treatment device, or placing leads or other medical devices.

Figure 6A:
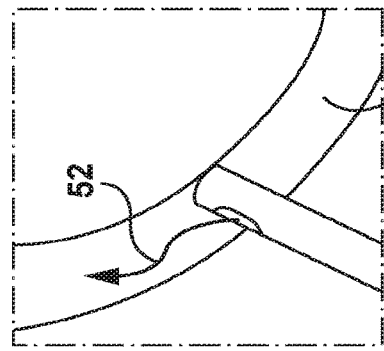
FIG. 6, consisting of FIGS. 6A-6E, is an illustration showing the steps in a method of using a needle in accordance with an alternative embodiment of the invention.
Figure 6B:
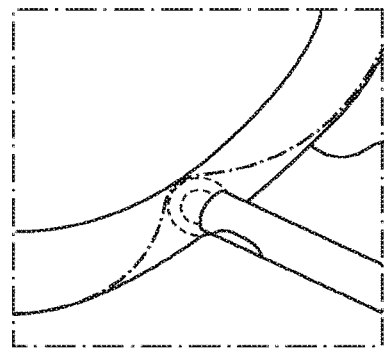
Figure 6C:
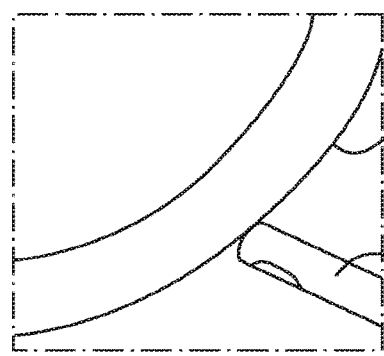
Figure 6D:
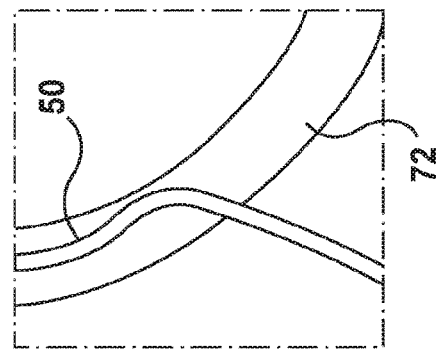
Figure 6E:
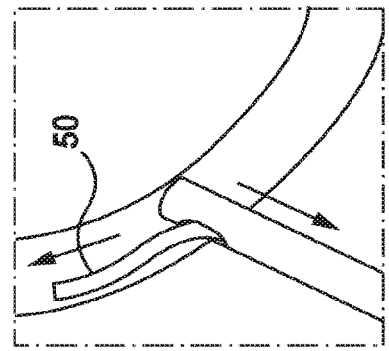

FIG. 6 is an illustration showing a five-step method of using two devices, needle 20 and guidewire 50. Step 1 (FIG. 6A) includes contacting a pericardium 70 using needle 20. Step 2 (FIG. 6B) includes tenting pericardium 70 with the needle and delivering energy (shown in broken line) through the blunt tip of needle 20. Step 3 (FIG. 6C) includes puncturing the pericardium 70 with the needle and injecting a contrast flow 52 into pericardial cavity 72 through a side-port of needle 20. FIG. 6D illustrates a step 4 of advancing a guidewire 50 through the needle and into pericardial cavity 72. After the guidewire 50 is advanced, the method further includes a step 5 of withdrawing needle 20 while leaving guidewire 50 in pericardial cavity 72 to arrive at the illustration of FIG. 6E. In some embodiments guidewire 50 has a diameter of about 0.032 inches (about 0.813 mm). As with the above method, once guidewire 50 has been advanced into pericardial cavity 72 to provide access, other steps may include advancing a mapping catheter or some other diagnostic device, advancing an ablation catheter or some other treatment device, or placing leads or other medical devices for example at the epicardium. Guidewire used in the two above described methods may have a straight tip or a curved tip.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A needle for use with a guidewire for gaining epicardial access, the needle comprising:
   an elongate member which is comprised of a metal and defines a lumen and a side-port having a proximal edge, the side-port being in fluid communication with the lumen;
   an insulation covering an outside of the elongate member wherein a blunt tip of the needle is electrically exposed to define an electrode for delivering energy for puncturing tissue, the insulation including an aperture and an insulation portion extending past the proximal edge of the side-port, wherein part of the elongate member adjacent the side-port is exposed within the aperture; and
   a guiding surface extending from a side wall of the elongate member opposite the side-port, the guiding surface configured to direct the guidewire from the lumen and out the side-port.

2. The needle of claim 1, wherein the needle is configured to deliver energy through a metal side wall of elongate member to the electrode.

3. The needle of claim 2, wherein the electrode has greater radiopacity than the elongate member.

4. The needle of claim 2, further comprising insulation on an inner surface of the elongate member adjacent to the side-port to reduce electrical leakage.

5. The needle of claim 2, further comprising insulation on an inner surface of most or substantially all the elongate member to reduce electrical leakage.

6. The needle of claim 2, wherein the part of the elongate member adjacent the side-port is distal of the side-port and is electrically exposed to define an elongate member exposed portion.

7. The needle of claim 1, wherein the insulation portion is configured to reduce abrasive friction between the device and the proximal edge of the side-port as the device is advanced through the side-port.

8. The needle of claim 1, wherein the side-port is capsule-shaped.

9. The needle of claim 1, wherein a distal edge of the side-port includes a bevel.

10. The needle of claim 9, wherein the bevel includes a combination of rounded and flat portions.

11. The needle of claim 1, wherein the proximal edge of the side-port is beveled proximally from an outer surface of the elongate member towards the lumen.

12. The needle of claim 1, wherein the guiding surface has a generally S-shaped surface.

13. The needle of claim 1, wherein a distal end of the guiding surface is beveled, whereby the insulation portion which covers a proximal part of the side-port and the distal end of the guiding surface facilitate the device being guided out of a side of the needle and in a forward direction when advanced out of the side-port.

14. A needle for use with a guidewire for gaining epicardial access, the needle comprising:
   an elongate member which is comprised of a metal and defines a lumen and a side-port having a proximal edge, the side-port being in fluid communication with the lumen;
   an insulation covering an outside of the elongate member wherein a blunt tip of the needle is electrically exposed to define an electrode for delivering energy for puncturing tissue, the insulation including an aperture and an insulation portion extending past the proximal edge of the side-port, wherein part of the elongate member adjacent the side-port is exposed within the aperture; and
   a guiding surface extending from a side wall of the elongate member opposite the side-port, the guiding surface configured to direct the guidewire from the lumen and out the side-port;
   wherein a distal end of the guiding surface is beveled so as to direct the guidewire in a distal direction upon exiting the side-port.

15. The needle of claim 14, wherein the needle is configured to deliver energy through a metal side wall of elongate member to the electrode.

16. The needle of claim 15, further comprising insulation on an inner surface of the elongate member adjacent to the side-port, the insulation configured to reduce electrical leakage.

17. The needle of claim 14, wherein the insulation portion is configured to reduce abrasive friction between the device and the proximal edge of the side-port as the device is advanced through the side-port.

18. The needle of claim 14, wherein the side-port is capsule-shaped.

19. The needle of claim 14, wherein a distal edge of the side-port includes a bevel.

20. The needle of claim 19, wherein the bevel includes a combination of rounded and flat portions.

* * * * *